United States Patent [19]

Lentz et al.

[11] Patent Number: 4,857,050
[45] Date of Patent: Aug. 15, 1989

[54] RATIOMETRIC AIR-IN-LINE DETECTOR

[75] Inventors: David Lentz; Larry Wilson, both of Poway; Curt Deckert, Santa Anna, all of Calif.

[73] Assignee: Fisher Scientific Company, Pittsburgh, Pa.

[21] Appl. No.: 100,218

[22] Filed: Sep. 23, 1987

[51] Int. Cl.$^4$ .......................................... A61M 31/00
[52] U.S. Cl. ...................................... 604/67; 604/122; 128/DIG. 13; 250/577
[58] Field of Search ................... 604/65, 66, 253, 122, 604/123, 67; 250/577; 73/55; 128/DIG. 13

[56] References Cited

U.S. PATENT DOCUMENTS

| | | | |
|---|---|---|---|
| 3,908,441 | 9/1975 | Virloget | 73/55 |
| 3,985,133 | 10/1976 | Jenkins et al. | 604/67 |
| 4,280,495 | 7/1981 | Lampert | 604/31 |
| 4,366,384 | 12/1982 | Jensen | 250/577 |
| 4,533,350 | 8/1985 | Danby et al. | 604/253 |
| 4,566,337 | 1/1986 | Smart | 250/577 |
| 4,673,820 | 6/1987 | Kamen | 604/253 |
| 4,681,569 | 7/1987 | Coble et al. | 604/253 |
| 4,703,314 | 10/1987 | Spani | 250/577 |
| 4,718,896 | 1/1988 | Arndt et al. | 604/253 |
| 4,733,095 | 3/1988 | Kurahaski et al. | 250/577 |
| 4,784,643 | 11/1988 | Siretchi et al. | 604/65 |
| 4,788,444 | 11/1988 | Williams | 250/577 |

OTHER PUBLICATIONS

Drop Detector, IBM Technical Bulletin, vol. 12, No. 5, Oct. 1969, E. R. Ellenwood.

Primary Examiner—C. Fred Rosenbaum
Assistant Examiner—Kathleen A. Daley
Attorney, Agent, or Firm—Nydegger & Harshman

[57] ABSTRACT

An air-in-line detector for use with an IV administration system comprises a light emitter positioned relative to a plurality of light sensors for receiving an IV tube therebetween. A comparator is connected with the light sensors to determine the relative intensity of light respectively incident on each sensor. Means connected with the comparator generates signals in accordance with the relative intensities to indicate whether an IV tube is present and, if so, whether there is fluid or air in the tube.

18 Claims, 3 Drawing Sheets

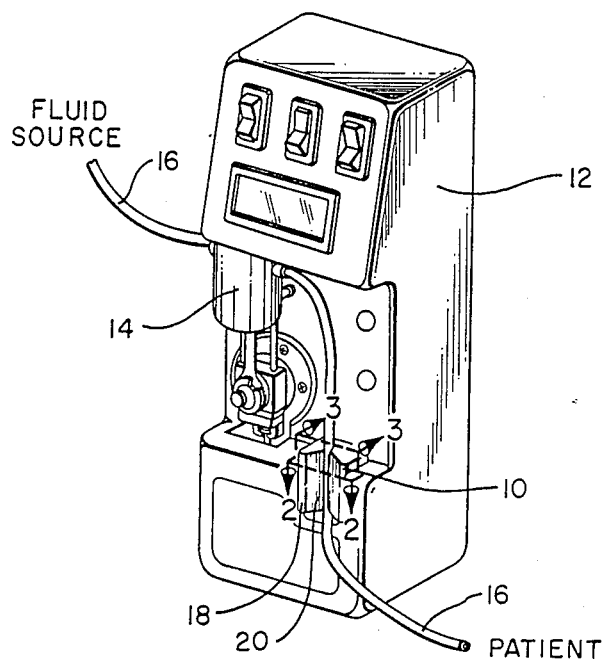
FIG. 1
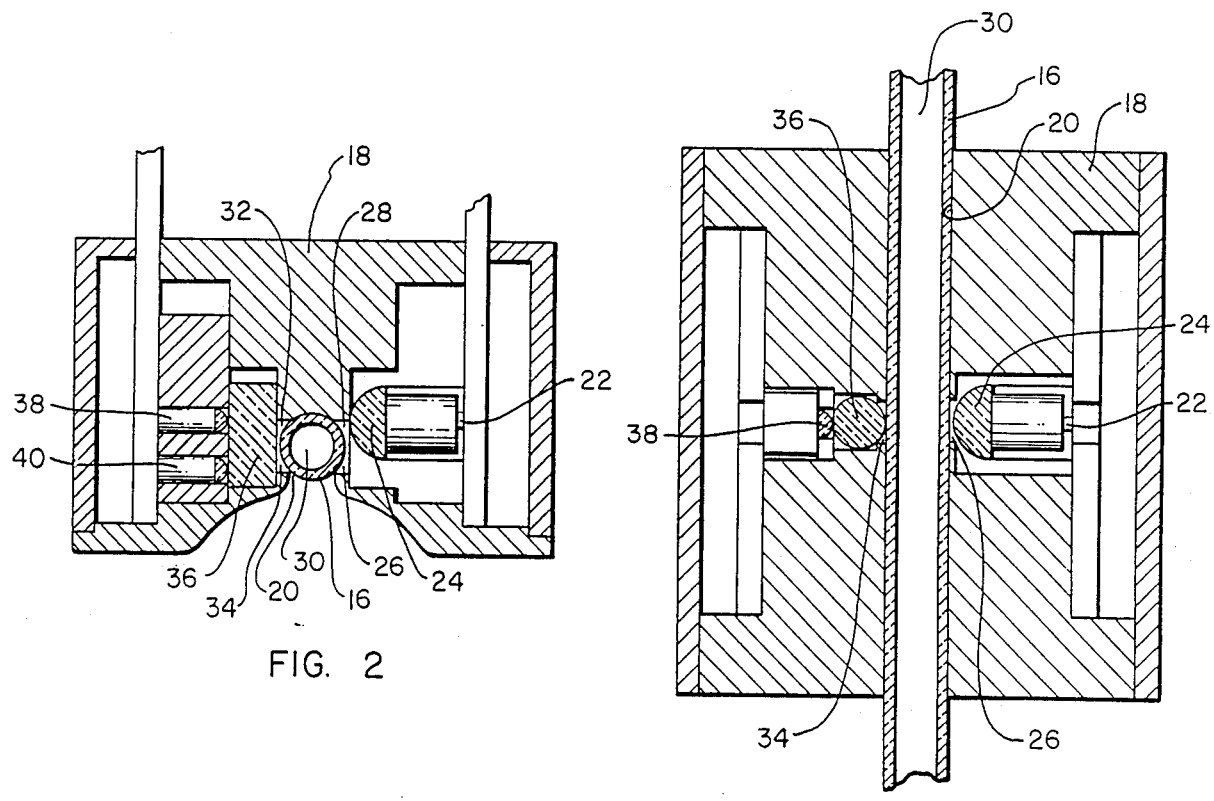
FIG. 2
FIG. 3

RATIOMETRIC AIR-IN-LINE DETECTOR

BACKGROUND OF THE INVENTION

This invention relates generally to air-in-line detectors used in cooperation with electronic devices to regulate or control the flow of fluid through a tube. More particularly, the present invention pertains to air-in-line detectors which sense alterations to a light path in response to fluid flow conditions in a fluid line. This invention is particularly, though not exclusively, useful in cooperation with electronic medical devices which are used for the IV infusion of medical solutions to a patient.

DESCRIPTION OF THE PRIOR ART

The use of air-in-line detectors with IV infusion devices is well known in the medical profession. Such detectors are recognized for providing a valuable safety feature which overcomes many of the problems and potential hazards that can be caused by the unwanted infusion of air into the human patient. As is to be expected, several methods for determining the presence of air-in-line conditions have been proposed. Specifically, ultra-sonics and optics have been used for this purpose. For example, U.S. Pat. No. 4,344,429 to Gupton discloses a flow metering apparatus and a bubble detector which uses light conditions for determining an air-in-line condition. To accomplish its purpose, Gupton relies on the focusing effect of the fluid in the fluid line, and interrupts operation of the infusion device whenever a lack of fluid attenuates the focusing effect and causes the light intensity level to fall below some predetermined level.

In a slightly different version of an optical apparatus for use in determining an air-in-line condition, U.S. Pat. No. 4,366,384 to Jensen discloses an air bubble detector which analyzes signals from a pair of optical sensors. The first optical sensor is associated for direct propagation of light through the tube and a second detector relies on the reflective ability of the IV tube's walls. U.S. Pat. No. 4,658,244 to Meijer which is assigned to the same assignee as the present invention discloses an air-in-line detector wherein a plurality of optical sensors are arranged along the tube and biased in a manner which allows for a logical determination of whether fluid is in the line.

Unlike the disclosures in the prior art, the present invention recognizes that an air-in-line condition can be indicated for an IV tube by the proper utilization of the refractive properties of the fluid within the tube. More specifically, the present invention recognizes that a single emitter can be properly positioned with respect to a plurality of sensors for the purpose of detecting the intensity of light falling on any one of the respective sensors and ratioing the intensities in accordance with a truth table to properly establish whether fluid is in the tube.

Accordingly, it is an object of the present invention to provide an air-in-line detector which is easily manufactured and which is dependable and reliable. Another object of the present invention to provide an air-in-line detector for an IV tube which is accurate and capable of distinguishing between the presence or absence of fluid in the IV tube. Yet another object of the present invention is to provide an air-in-line detector having a self-test operation which insures safe operation of the detector. It is still another object of the present invention to provide an air-in-line detector which is cost effective.

SUMMARY OF THE INVENTION

The preferred embodiment of this invention includes a base formed with a channel for receiving a resilient transparent fluid tube therein. A light emitter is mounted on one side of the channel and two juxtaposed light sensors are mounted on the opposite side of the channel and positioned to receive light from the emitter. Lenses may be positioned in the light path between the emitter and the light sensors to effectively direct light therebetween in accordance with the purposes of the present invention. A comparator is electronically connected with each light sensor to obtain signals therefrom that correspond to the intensity of light received by the respective sensors. Both comparators are connected with electronic logic circuitry which ratios the signals from the sensors to determine whether a tube is present in the channel and, if so, whether there is air or fluid in the tube.

The preferred embodiment of this invention also includes a self-test circuit which insures the air-in-line detector is properly working. This self-test circuit includes a second light emitter which is positioned to direct the preponderance of its light onto that sensor which receives the higher intensity of light when there is an air-in-line condition. A strobed input causes alternating emissions from the two light emitters with the result that proper operation is indicated when an air-in-line condition is indicated during the time light is emitted from the second emitter.

The novel features of this invention, as well as the invention itself, both as to its organization and operation will be best understood from the accompanying drawings, taken in conjunction with the accompanying description, in which similar reference characters refer to similar parts, and in which:

BRIEF DESCRIPTION OF THE DRAWINGS

FIG. 1 is a perspective view of the detector of the present invention mounted on an IV infusion device;

FIG. 2 is a cross-sectional view of the detector as seen along the line 2—2 in FIG. 1;

FIG. 3 is a cross-sectional view of the detector as seen along the line 3—3 in FIG. 1;

DESCRIPTION OF THE PREFERRED EMBODIMENT

Figure 4:
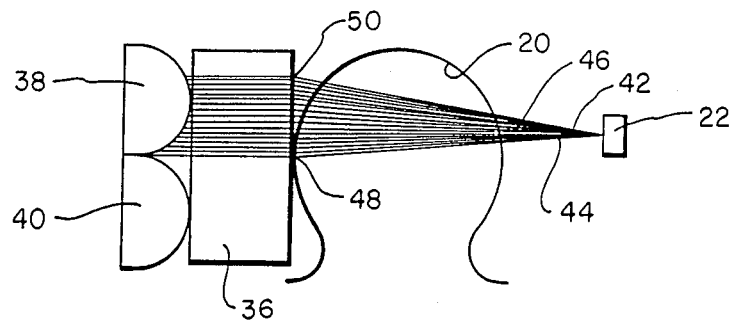
FIG. 4 is a schematic representation of the light path for the detector without tubing present.

Referring now in detail to the drawings. The air-in-line detector 10 of the present invention is shown in FIG. 1 mounted on an IV infusion device 12 which is intended to provide means for infusing IV solutions through an IV tube 16 from a fluid source (not shown) to a patient (not shown). IV depending upon the purposes of IV infusion device 12, may either be a pumping chamber or an IV tube restrictor. Incorporated into IV infusion device 12 is the air-in-line detector 10 of the present invention. As shown in FIG. 1, air-in-line detector 10 comprises a base 18 which is formed with a channel 20 for receiving and holding IV tube 16.

In FIG. 2, the interaction of structure for various components of air-in-line detector 10 in its association with an IV tube 16 is clearly shown. As previously disclosed, base 18 is formed with a channel 20 into which IV tube 16 can be positioned. Mounted on base 18, is a light emitter 22. In accordance with teachings of the pertinent art, light emitter 22 can be a light emitting diode (LED) which emits light energy in the infra-red range. Light emitter 22 can also be any light source known by skilled artesans to be suitable for the purposes of the present invention. It will be understood that light from light emitter 22 passes through a lens 24 which is preferably plano-convex in structure and designed to concentrate or focus light energy emanating from light emitter 22. After being focused by lens 24, light from emitter 22 passes through aperture 26, which is formed on side 28 of the channel 20, and then through the channel 20. As shown in FIG. 2, an IV tube 16 having a lumen 30 through which fluids may pass is positioned within the channel 20.

Opposite from side 28 of channel 20 is a side 32 of channel 20 which is formed with an aperture 34 through which light from the emitter 22 may pass. After passage through 24 aperture 34, the light is focused by a cylindrical shaped lens 36 and directed toward a light sensor 38 which is mounted on base 18 on the side of channel 20 opposite from emitter 22. Juxtaposed with light sensor 38, is a light sensor 40. It is to be understood that more than two sensors may be employed by the present invention. The present invention, however, can be practiced and adequately described using only two such sensors. Importantly, light sensor 38 and light sensor 40 are juxtaposed so that the preponderance of light energy received from emitter 22 can be shifted from one to the other with only a minimal deflection in the path of the light. As will be discussed and disclosed below in more detail, it is not so important that the sensors 38, 40 alternatively receive light Instead, with the present invention, it is important to determine which of the light sensors 38 or 40 is receiving the relatively greater amount of light energy emanating from light emitter 22.

FIG. 3 shows a cross section of the air-in-line detector 10 from a perspective 90° in rotation from the presentation of FIG. 2. The comparison of FIGS. 2 and 3 perhaps more clearly indicates the actual cooperation of structure between the various elements. In FIG. 3 it is seen that light emitter 22, as mounted on base 18, passes light energy through lens 24, where the energy is focused and further passed through aperture 26. It is also seen in FIG. 3 that the IV tube 16, as mounted in channel 20, presents an obstacle for the passage of light between emitter 22 and the receiver 38. After passage through the IV tube 16, light enters aperture 34 and passes through lens 36 before it is incident on light sensor 38. Importantly, aperture 34 is of sufficient size to allow enough light energy to pass therethrough to overcome any blocking effect small particles in the fluid line may have on the beam of light. It is also important to the present invention that the direct light path between emitter 22 and sensor 38 not pass through the center of tube 16. For reasons well known by the skilled artisan, there needs to be an axial offset between the longitudinal axis of tube 16, as it is mounted in channel 20, and the direct path of light from emitter 22 to sensor 38. Stated differently, in their relation to tube 16, neither sensor 38 nor sensor 40 are positioned diametrically opposite from emitter 22. This is so in order to allow the refractive property of the fluid in tube 16 to be effectively used.

Figure 5:
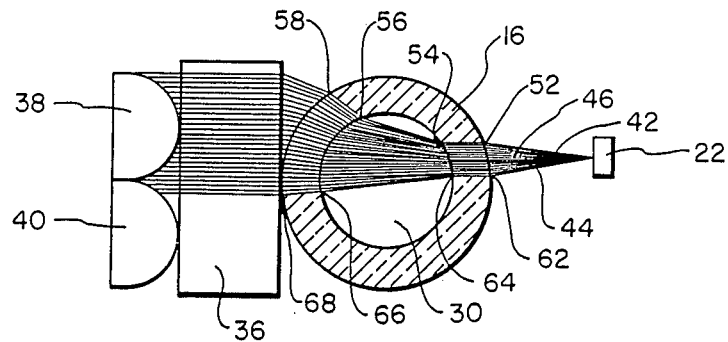
FIG. 5 is a schematic representation of the light path for the detector with tubing present under an air-in-line condition.
Figure 6:
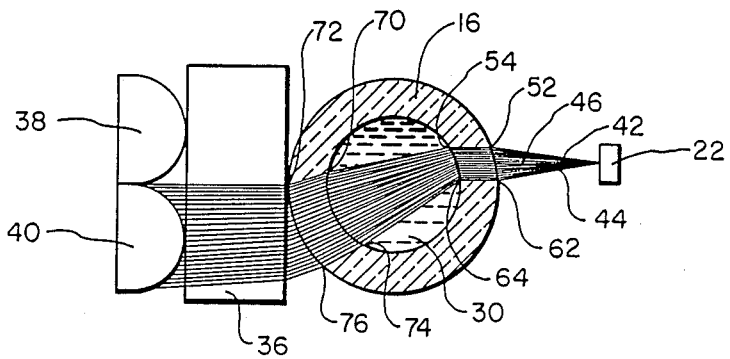
FIG. 6 is a schematic representation of the light path for the detector with tubing present under a fluid-in-line condition.

FIGS. 4, 5 and 6 are schematic drawings of the path of light rays between emitter 22 and the light sensors 38 and 40 for differing conditions. FIG. 4 is a schematic representation of light rays within the air-in-line detector 10, in a no tubing condition, i.e. a condition in which IV tube 16 is not positioned within channel 20. FIG. 5 shows the condition where an IV tube 16 is positioned in channel 20, but no fluid is in IV tube 16. FIG. 6 represents the condition where there is fluid within tube 16 which shifts the light from emitter 22 onto sensor 40 substantially as shown. A more detailed understanding of the physical characteristics of these conditions can be had by initial reference to FIG. 4.

In FIG. 4 it is seen that the beam of light 46 from emitter 22 is defined by the ray of light 42, and the ray of light 44. Although lens 24 is not shown in FIGS. 4, 5 and 6 it is to be understood that lens 24 when incorporated does not affect the schematic representation of the conditions portrayed in these figures. Thus, rays 42 and 44 represent the boundary of light beam 46 as it travels between emitter 22 and the sensors 38 and 40. In FIG. 4, for the condition where no IV tube 16 is present within channel 20, rays 42 and 44 defining the envelope of beam 46 are unaffected after leaving emitter 22 until they are incident on lens 36 at respective points 50 and 48. After being focused by lens 36, beam 46 strikes sensor 38. Possibly, a small portion of sensor 40 also receives some light energy. This really is of no moment. What is important, however, is that sensor 38 receive more light than sensor 40.

Unlike the no-tube condition, the condition shown in FIGS. 5 and 6 result from the refraction of light. For purposes of describing the propagation of light as it travels from one medium to another, recall the law of refraction which states that the ratio of the sine of the angle of incidence ($\phi$) to the sine of the angle of refraction ($\phi'$) is equal to the ratio of the velocities in the two media. Since the velocities are constants, their ratio is also constant. Thus:

$$\frac{\sin \phi}{\sin \phi'} = \text{constant}$$

This basic relationship describes the bending of transmitted light as it refracts upon passage from one medium to another. It does not describe the behavior of reflected light. The present invention, however, is not concerned with reflected light.

Now, contrast the no tubing condition described above and shown in FIG. 4 with the condition portrayed in FIG. 5 where an empty tube 16 is placed in the path of light beam 46. Again, for purposes of discussion, consider beam 46 to be bounded by light rays 42 and 44. Also, recall that the centerline of beam 46 is axially offset from the longitudinal axis of tube 16. Under the condition shown in FIG. 5, beam 46 will pass from one medium to another four different times after leaving emitter 22 before it is incident on lens 36. Specifically, while enroute on this path, beam 46 will pass from air to tubing, to air, to tubing and again to air. At each transition the beam will be refracted. More specifically, rays 42, 44 are respectively refracted at points 52, 62 as they strike tubing 16. This is followed by subsequent respective refractions at points 54, 64 where they emerge from the side wall of tube 16 into lumen 30. Refraction again occurs at the medium interface between points 56, 66 and at the medium interface between points 58, 68 as beam 46 emerges from tube 16. Thereafter, beam 46 is focused by lens 36 for incidence on sensor 38 and part of sensor 40 substantially as shown in FIG. 5.

With fluid in tube 16, the refractive index between tube 16 and the fluid in lumen 30 causes beam 46 to be shifted into a path substantially as shown in FIG. 5. Specifically, as beam 46 emerges from tube 16 at points 54, 64, beam 46 is refracted to direct light between points 70, 74 for further refraction at points 72, 76 as the beam 46 leaves tube 16. The shift occurs, in part, due to the fact that light from emitter 22 is not focused through the centerline of tube 16. Thereafter, like the air-in-line condition depicted in FIG. 5, beam 46 is focuses by lens 36 for incidence on sensors 38 and 40 substantially as shown in FIG. 5.

When comparing the fluid-in-line condition of FIG. 6 with either the no tube condition of FIG. 4 or the air-in-line condition of FIG. 5 it can be seen that with fluid in the line beam 64 is shifted so as to be predominantly incident upon light sensor 40. This shift causes a change in the electronic signals generated by the sensors 38 and 40 which can be used for a logic determination to indicate a fluid-in-line condition.

Figure 7:
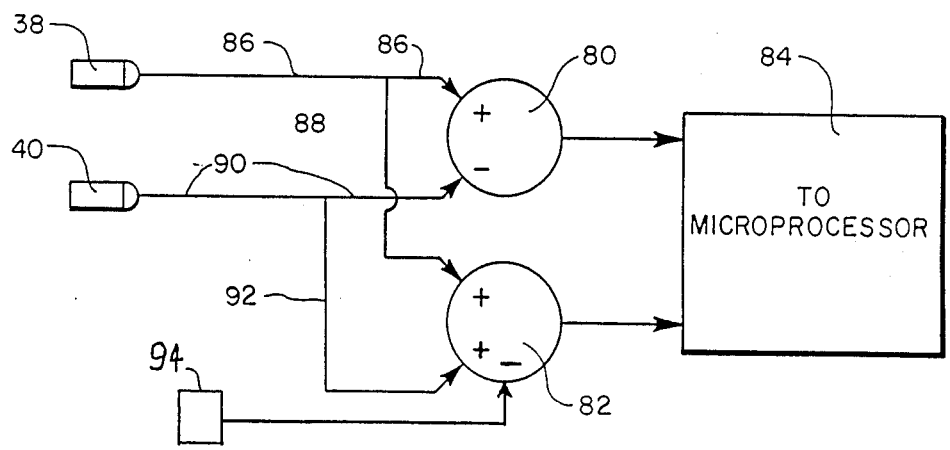
FIG. 7 is a schematic representation of the logic circuitry of the detector.

The pertinent electronic circuitry of the present invention will be best appreciated by reference to FIG. 7, wherein it is seen that light sensors 38 and 40 are each electronically connected to both comparators 80 and 82. As shown, comparators 80 and 82 are electronically connected with a micro-processor 84 wherein the actual computations, calculations and logic manipulations are made. It will be understood that any micro-processor well known in the pertinent art can be adapted for use with the present invention depending on the particular needs and desires of the operator.

As indicated above, FIG. 7 shows that light sensor 38 and light sensor 40 each has electrical connections to both of the comparators 80 and 82. More specifically, it will be seen that receiver 38 is electronically coupled to comparator 80 via connector 86 and to the comparator 82 by connector 88. Additionally, light sensor 40 is electronically coupled to the comparator 80 via connector 90 and to comparator 82 via connector 92.

A voltage source acting as a reference 94 is electronically connected to comparator 82 to establish a threshold. As long as the sum of the inputs to comparator 82 is above the threshold established by reference 94, microprocessor 84 evaluates the input from comparator 80. With this input, microprocessor 84 makes its logic manipulations to determine the state of operation of device 12. On the other hand, when the sum of the inputs to comparator 82 from sensors 38 and 40 fall below the threshold established by reference 94, microprocessor 84 no longer evaluates input from comparator 80. Instead, microprocessor 84 considers there is an opaque fluid in IV tube 16.

Figure 8:
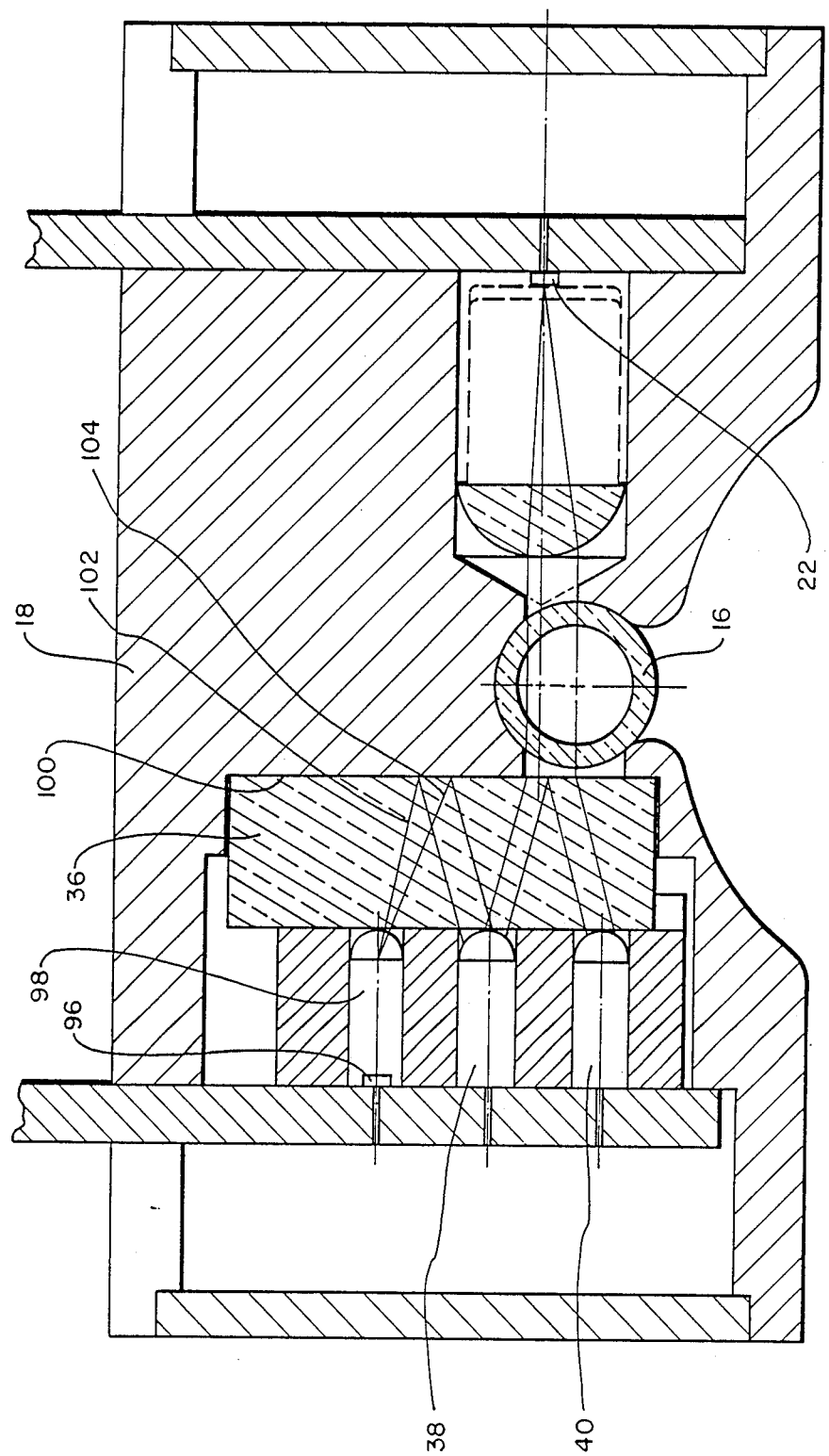
FIG. 8 is a cross-sectional view of the detector having a second light emitter for use in a self-test operation as seen along the line 2—2 in FIG. 1.

The self-test capability for detector 10 of the present invention is made possible by the incorporation of a second light emitter 96. As shown in FIG. 8, second light emitter 96 is mounted on base 18 and juxtaposed wit light sensor 38 so that light sensor 38 is positioned between light emitter 96 and light sensor 40. It will be appreciated by the skilled artesan that the self-test capability for detector 10 can be accomplished with any relative positioning between emitter 96 and sensor 38 so long as light emitted from emitter 96 can be directed to be incident on sensor 38. The configuration of elements as shown in FIG. 8 is preferred.

According to the preferred embodiment, light from second emitter 96 passes through a lens 98 for further passage through the lens 36. During its transit of lens 36, light from emitter 98 is reflected off surface 100 of base 18 and directed toward light sensor 38. Light rays 102 and 104 shown in FIG. 8 are representative of the light emitted by emitter 96 and generally define the boundaries of the light beam which in its functional orientation as an element of the self-test circuit.

The need for a self-test capability stems from the fact that if sensor 38 fails and becomes inoperative, comparator 80 will not receive input from sensor 38. It will, however, still receive input from sensor 40. Microprocessor 84 sees such a comparative reception as indicative of a fluid-in-line condition. Importantly, this can occur even when there is actually an air-in-line condition. Obviously, this false indication will not happen if sensor 38 is operational. Therefore, the self-test logic of detector 10 is predicated on a check of the operational capacity of sensor 38.

OPERATION

In its operation air-in-line detector 10 must distinguish between four separate conditions. These are: (i) tube 16 not mounted on device 12, (ii) air-in-line, (iii) clear fluid-in-line, and (iv) opaque fluid-in-line. During normal operation under the first three conditions, i.e. all but when an opaque fluid is in tube 16, some light from emitter 22 will be incident on either one or both of sensors 38, 40. Therefore, under these three conditions, comparator 82 will indicate that the summed signal of intensities from sensors 38, 40 is above the predetermined level established by reference 94. On the other hand, when an opaque fluid is present in conduit 30 of tube 16 this summed signal will drop below the predetermined level because light from emitter 22 will be blocked by the opaque fluid. Thus, according to well-known techniques in the pertinent art, microprocessor 84 can be programmed to identify this condition and thereby distinguish an opaque fluid-in-line condition from the other three conditions. To distinguish between these other three conditions, microprocessor 84 uses input from comparator 80.

As best shown in FIG. 7, signals from both sensors 38 and 40 provide input to comparator 80. In contrast to the condition where opaque fluid is flowing through lumen 30 of tube 16 to block light from emitter 22, under conditions (i), (ii) and (iii) set forth above, light from emitter 22 will activate sensor 38 and 40 in varying degrees. The relative intensity of such activation can be used as meaningful input to comparator 80. It happens that of the three conditions only the clear fluid-in-line condition, i.e. condition (iii), needs to be distinguished from the other two since if either tube 16 is not connected with device 12, or there is an air-in-line condition, the device 12 should not be operating. For the present invention this distinction is made by determining whether sensor 38 or sensor 40 is receiving the preponderance of light energy from emitter 22. This process is easily visualized by comparing FIGS. 4 and 5 with FIG. 6. FIG. 6 shows that beam 46 is refracted by fluid in tube 16 and directed, after refraction, to strike predominantly on sensor 40. On the other hand, as shown respectively in FIGS. 4 and 5, when there is no tube 16 in channel 20, or there is an air-in-line condition, beam 46 is not refracted by fluid and consequently strikes predominantly on sensor 38. This phenomenon generates different electronic inputs to comparator 80 depending on whether there is a fluid-in-line condition.

In those cases where either an opaguefluid or a clear fluid is in tube 16, microprocessor 84 should recognize it as normal operation and be programmed for continued functioning of the IV infusion device 12. On the other hand, an indication from comparator 80 of either an air-in-line condition or a tube-not-installed condition should be used to cause IV infusion device 12 to alarm and cease operation.

The logic used for the self-test capability of detector 10 is compatible with the logic previously discussed. Specifically, the same electronic circuitry schematically shown in FIG. 7 is used. In order to use this circuitry for the self-test operation, however, both light emitters 22 and 96 must be used and alternatingly activated. This requires a strobed input to both emitters using electronic components (not shown) which are well known in the pertinent art.

With light alternatingly being emitted from emitters 22 and 96, the logic of the self-test circuit is best understood by considering each condition separately. When emitter 22 is activated and emitter 96 is deactivated, the electronic circuitry shown in FIG. 7 functions to distinguish between the four conditions in a manner as previously disclosed. The self-test logic is initiated when emitter 96 is activated and emitter 22 is deactivated. As best seen in FIG. 8, when emitter 96 is activated the focus effect of lens 36 will cause the preponderance of light reflected off surface 100 to fall on sensor 38. If sensor 38 is operative, this circumstance will cause comparator 80 to sense a comparative input from sensors 38 and 40 which is indicative of an air-in-line condition. On the other hand, if sensor 38 has failed and is inoperative, sensor 40 will apparently receive more light from emitter 96 than it does from sensor 38. In this case, comparator 80 will sense a comparative input from sensors 38 and 40 which is indicative of a fluid-in-line condition. Microprocessor 84 can be programmed to use these different inputs for the purpose of determining the operability of sensor 38. Specifically, if comparator 80 senses a fluid-in-line condition during the interval when emitter 96 is activated and emitter 22 is deactivated, microprocessor 84 will consider sensor 38 to be inoperative. Further, microprocessor 84 can be programmed to activate alarm circuitry in the event sensor 38 is determined to be inoperative.

It will be noted that the positioning of emitter 96 in relation to sensor 38 is such that the light transmitted therebetween does not pass through tube 16. Consequently, the self-test capability of detector 10 is independent of the physical characteristics of tube 16 and of the fluid passing therethrough.

While a particular air-in-line detector as herein shown and disclosed in detail is fully capable of obtaining the objects and providing the advantages herein before stated, it is to be understood that it is merely illustrative of the presently preferred embodiments of the invention and that no design herein shown other than those described in the amended claims.

We claim:

1. An IV tube air-in-line detector comprising:
a first light emitter;
a receiver having juxtaposed first and second sensor means for independently sensing the intensity of light from said emitter respectively incident thereon;
means for holding said emitter and said receiver with said tube therebetween;
a first comparator electronically connected with said first and second sensor means to indicate an air-in-line condition when the intensity of light incident on said first sensor means is more than the intensity of light incident on said second sensor means and to indicate a fluid-in-line condition when the intensity of light incident on said second sensor means is more than the intensity of light incident on said first sensor means;
a second emitter mounted on said holding means to transmit light from said second emitter to said first sensor means; and
a strobe means electrically connected to said first and second light emitters to alternatingly cause light emissions from said first and second light emitters.

2. An IV tube air-in-line detector as cited in claim I further comprising means electrically connected with said first sensor means to determine whether said first sensor means receives light from said second light emitter.

3. An IV tube air-in-line detector as cited in claim 2 wherein said second light emitter is juxtaposed with said receiver to place said first sensor means between said second light emitter and said second sensor means; and further comprising means positioned on said holding means to reflect light from said second light emitter onto said first sensor means.

4. An IV tube air-in-line detector as cited in claim 3 wherein light from said light emitter is collimated light.

5. An Iv tube air-in-line detector as cited in claim 4 wherein said light emitter is not diametrically opposed from said receiver relative to said tube.

6. An IV tube air-in-line detector as cited in claim 5 wherein said holding means is formed with a channel for receiving said tube therein.

7. An Iv tube air-in-line detector as cited in claim 6 wherein light from said light emitter is infra-red light.

8. An IV tube air-in-line detect as cited in claim 7 wherein said IV tube is transparent.

9. An IV tube air-in-line detector as cited in claim 8 further comprising a second comparator for indicating a fluid-in-line condition when the sum of the intensities of said first and said second sensing means is below a predetermined level.

10. An IV tube air-in-line detector comprising:
a first light emitter;
a first light sensor for receiving light from said emitter;
a second light sensor juxtaposed with said first light sensor for independently receiving light from said emitter;
means of hold said tube between said emitter and said first and second sensors; and
means for determining the ratio of the intensity of light received by said first sensor to the intensity of light received by said second light sensor to indicate an air-in-line condition when the ratio of intensities is substantially greater than unity, and to indicate a fluid-in-line condition when the ratio is substantially less than unity or the sum of the intensities is below a predetermined level;

a second emitter mounted on said molding means to transmit light from said second emitter to said first sensor means; and a strobe means electrically connected to said first and second light emitters to alternatingly cause light emissions from said first and second light emitters.

11. An IV tube air-in-line detector as cited in claim 10 further comprising means electrically connected with said first sensor means to determine whether said first sensor means receives light from said second light emitter.

12. An IV tube air-in-line detector as cited in claim 11 wherein said second light emitter is juxtaposed with said receiver to place said first sensor means between said second light emitter and said second sensor means; and further comprising means positioned on said holding means to reflect light from said second light emitter onto said first sensor means.

13. Iv tube air-in-line detector as cited in claim 12 wherein light from said light first emitter is collimated.

14. An IV tube air-in-line detector as cited in claim 13 wherein said light emitter and said juxtaposed first and second light sensor are to diametrically disposed relative to said tube.

15. An IV tube air-in-line detector as cited in claim 14 wherein said holding means if formed with a channel for receiving said tube therein.

16. An IV tube air-in-line detector as cited in claim 15 wherein light from said first light emitter is infra-red.

17. An IV tube air-in-line detector as cited in claim 16 wherein said IV tube is transparent.

18. A method for indicating an air-in-line condition for an IV tube comprising the steps of:

holding said tube in the path of collimated light between a strobed light emitter and a pair of juxtaposed light sensors;

ratioing the intensity of light incident on said light sensors;

indicating an air-in-line condition when the ratio is within a predetermined range;

disregarding the ratio and indicating a fluid-in-line condition whenever the sum of intensities from said light sensors falls below a predetermined level; and aiming light from a second strobed light emitter in alternation with said strobed light at one of said pair of light sensors to check operation of said ratioing step.

* * * * *